United States Patent [19]

Meyer

[11] Patent Number: 5,779,683
[45] Date of Patent: Jul. 14, 1998

[54] INJECTOR MODULE FOR A SYRINGE AND PRE-FILLED SYRINGE PROVIDED THEREWITH

[75] Inventor: Gabriel Meyer, Dully, Switzerland

[73] Assignee: Medicorp Holding S.A., Luxembourg, Luxembourg

[21] Appl. No.: 532,704

[22] PCT Filed: Feb. 7, 1995

[86] PCT No.: PCT/IB95/00080

§ 371 Date: Nov. 29, 1995

§ 102(e) Date: Nov. 29, 1995

[87] PCT Pub. No.: WO95/21647

PCT Pub. Date: Aug. 17, 1995

[30] Foreign Application Priority Data

Feb. 14, 1994 [CH] Switzerland ................. 429/94

[51] Int. Cl.⁶ ................................................. A61M 5/32
[52] U.S. Cl. ................................................ 604/118; 604/110
[58] Field of Search ............................. 604/198, 86–89, 604/200, 201, 205, 195–197, 187, 110, 232, 192

[56] References Cited

U.S. PATENT DOCUMENTS

| | | |
|---|---|---|
| 2,571,653 | 2/1951 | Bastien. |
| 3,785,379 | 1/1974 | Cohen ................. 604/88 |
| 4,425,120 | 1/1984 | Sampson et al.. |
| 4,573,976 | 3/1986 | Sampson et al.. |
| 4,631,057 | 12/1986 | Mitchell ............ 604/198 |
| 4,738,663 | 4/1988 | Bogan. |
| 4,790,827 | 12/1988 | Haber et al. ....... 604/198 |
| 4,927,417 | 5/1990 | Moncada et al.. |
| 4,994,045 | 2/1991 | Ranford. |
| 5,057,087 | 10/1991 | Harman ............. 604/198 |
| 5,061,251 | 10/1991 | Jubasz. |
| 5,197,953 | 3/1993 | Colonna ............ 604/110 |
| 5,328,485 | 7/1994 | Moreno et al. ..... 604/198 |

FOREIGN PATENT DOCUMENTS

| | | |
|---|---|---|
| 0 281 421 | 9/1988 | European Pat. Off.. |
| 0 288 879 | 11/1988 | European Pat. Off.. |
| 0 331 452 | 9/1989 | European Pat. Off.. |
| 2 300 578 | 9/1976 | France. |
| 2617718 | 1/1989 | France. |
| 88 02 080 | 5/1988 | Germany. |
| WO 93/00942 | 1/1993 | WIPO. |

Primary Examiner—Michael Buiz
Assistant Examiner—A. T. Nguyen
Attorney, Agent, or Firm—Davis and Bujold

[57] ABSTRACT

An injector module (40) and a one- or two-component syringe comprising the same. the module including a cylindrical barrel (41), a needle (43) extending from the end thereof. and a protective sleeve (42) for said needle. The sleeve consists of a single rigid member axially slidable over the cylindrical barrel (41). The cylindrical barrel is provided with a skirt (46) with at least one flexible tab (47) engageable with an inner ring-shaped rib (50) of the rigid cylindrical sleeve to prevent the return of the sleeve once it has been moved forward. For this purpose, the flexible tabs (47) comprise a slanted end (47a) and a rounded edge (47b) which engage said inner rib.

18 Claims, 13 Drawing Sheets

INJECTOR MODULE FOR A SYRINGE AND PRE-FILLED SYRINGE PROVIDED THEREWITH

The present invention concerns an injector module consisting of a syringe sub-assembly, said module comprising a cylindrical barrel, a needle extending from the proximate extremity of the barrel and a protective sleeve for the needle, which is cylindrical and coaxial with the barrel, said sleeve being slidable between the retracted position, exposing the needle, and the advanced position, concealing the needle.

It also concerns a pre-filled syringe with one or two compartments containing at least one medicinal substance or a component of a medicinal substance to be reconstituted by mixing with another component, said syringe containing on the one hand, an injector module comprising a cylindrical barrel, a needle extending from the proximate extremity of the barrel, and a protective sleeve for the needle, which is cylindrical and coaxial with the barrel, said sleeve being slidable between a retracted position, exposing the needle, and an advanced position, covering the needle; and on the other hand, a propulsion-receptacle module comprising at least one receptacle defining the compartment or compartments holding the medicinal substance or the component of a medicinal substance, and at least one stopper associated with said receptacle, said stopper being slidable within the receptacle so that it acts as a piston, and said receptacle being slidable inside the barrel so that it acts as a piston shaft.

Both the Food and Drug Administration (FDA) and the American Society of Hospital Pharmacists (ASHP), the official United States agencies which control and establish regulations governing medicinal substances and how they are dispensed, recommend using injection systems with a needle which retracts inside the system after use, although this is not a requirement at present. This also the preference of the pharmacological industry and hospitals, particularly medical personnel. A legitimate fear of contracting certain viral illnesses has led doctors and nurses to use extreme precaution to avoid accidental contamination caused by being pricked with a used syringe or the like.

Numerous systems have been devised in an attempt to protect medical practitioners from accidental injuries. Even as early 1931, U.S. Pat. No. 1,921,034 proposed such a system. A syringe inside a receptacle formed of two telescoping elements was used for injections with the user having no contact at all with the needle, even accidentally. As a result, the principle of the retractable needle has been known in the art since at least that time.

U.S. Pat. No. 2,571,653 issued in 1951 describes a syringe with a barrel initially engaged in a sleeve which covers the needle and allows it to be manipulated without danger. At the time of use, the sleeve can be retracted from the needle barrel, making the needle visible and readying the syringe for use.

The disadvantage with all these systems is that the needle is never completely, effectively, and irreversibly protected after use. Current protective measures consist primarily of a sleeve surrounding the hypodermic syringe and the needle during storage, with the needle being extended at the time of use. They offer no provision for the needle retracting after injection of a patient in order to protect medical personnel.

Other embodiments derived from these devices are the subject of U.S. Pat. Nos. 4,738,663, 4,631,057, 4,573,976 and 4,425,120, which describe various guards for hypodermic syringes known in the art.

In particular, the system described in U.S. Pat. No. 5,061,251 attempts to overcome this problem. To accomplish this, the system has a spring associated with a piston shaft; when the spring is compressed, it pushes the needle out of the protective sleeve. In order for the system to work, the friction of the piston inside the syringe barrel must be greater than the restraining force exerted by the spring, or the medicinal substance would be evacuated from the syringe before injection. The piston can only begin to displace and force the injectable substance toward the needle when the spring is blocked. The counter-reaction exerted by the spring is constant and tends to make the needle retract inside the sleeve. Because of this, it is not possible to aspirate solution with this syringe. Therefore, the "vein test" operation, which consists of aspirating some blood from the patient just before injection to verify that the needle is properly implanted in a vein, is possible only with some difficulty. The user must compress the spring and keep it contracted with one hand, and pull on the piston shaft to perform the aspiration with the other hand.

The system described in French Patent Application Publication No. 2 617 718 proposes a solution to the problem of how to protect the needle before and after injection when using a pre-filled syringe.

During storage, needle sterility is ensured because a truncated portion of a protective sheath cooperates with a truncated portion of a sleeve under pressure from a spring which, however, is presumably extended. The slightest pressure on the protective sheath causes the truncated elements to separate, and the needle therefore communicates with the outside of the syringe. Thus, needle sterility is easily destroyed, and nothing is provided to prevent this type of accident.

To perform the injection, the user must apply the end of the protective sheath firmly against the patient's skin.

Considerable force must be applied to simultaneously push the needle through the bottom wall of the sheath, compress the spring tightly, and eject the sleeve so it contacts the piston and expels the solution.

All these forces are exerted directly on the patient's skin, resulting in the expected marks and hematomas, so the patient experiences continuous pain during the injection, etc. When the operator stops exerting constant, progressive pressure on the base of the syringe container, the injection is interrupted and the protective shaft again covers the needle, dislodging it from the injection position in the patient's skin. A vein test is impossible to perform. After the injection is either completed or accidentally interrupted, the needle is not irreversibly protected by the detente action of the spring connected to the protective shaft. Actually, the least pressure upon the shaft causes the needle to reappear, and the system therefore offers medical personnel no dependable protection. The risk of accidental contamination is obvious.

Other embodiments are illustrated in European Publications EP 0 288 879 and EP 0 331 452, describing syringes with a barrel and a sleeve protecting the needle, which slides into an advanced position after the syringe is used. The syringe body comprises rigid ramps and the sleeve protecting the needle, which is actually a sleeve designed to protect the user from an accidental needle stick after use, has flexible tabs which cooperate with the ramps so that the sleeve snaps into place and locks.

Such "rigid ramp" systems make it very difficult to assemble the protective sleeve at the front of the syringe body. Because of the rigid ramp, the unit must be assembled as one piece by elastically deforming the sleeve so it can pass over the ramps and the stops. A sleeve cannot be flexible and still be blocked in the advanced position. If the sleeve is flexible enough for assembly, the anti-return function is not reliable. If the sleeve is too rigid, or if the difference in diameter between the interior sleeve and the exterior barrel create a tight seal between these two elements to guarantee the anti-return feature, considerable force is required for the sleeve to pass the rigid barrel ramps, either during assembly or during the advanced positioning stage. This is unacceptable. The blocking means may be damaged during assembly and/or the unit may require so much strength on the part of the operator that it is not convenient to use.

Furthermore, there is no provision for eliminating the flanges on the barrel so that the syringe could be pre-filled and manufactured at high speeds. The flanges actually make it impossible to group syringes into packets and process all the units in a packet simultaneously, so it becomes necessary to transport the syringes individually from the assembly or filling station to another work station.

In addition, there is no way to assemble the sleeve and the barrel without risking damage to the blocking elements, nor to eliminate the inevitable excessive friction caused when the sleeve passes the ramps as the operator places it in the advanced position. Likewise, there is no provision for guiding the sleeve and maintaining it in the barrel extension when it is in the advanced position.

Moreover, since the guard is designed to be flexible as it passes the rigid ramps, it is not possible to provide a rigid interior annular rib which would irreversibly lock the device in the advanced position irrespective of the exterior syringe barrel diameter. Such a design might possibly function, but only with large diameter syringes. This disadvantage is reinforced by the fact that the guard to be attached to the syringe barrel tapers on the proximate side. The tapered design makes it impossible to form a rigid interior rib with acute angles because a counter strip molding technique is generally used.

Thus, all the systems known in the art have limited utility, and furthermore, none uses syringes that are sterilized and pre-filled during assembly and manufactured at high speed by standard equipment.

The present invention overcomes these disadvantages with a system that allows high speed production, and therefore is responsive to current storage, transfer and utility requirements of the pharmaceutical industry. It also can be used to inject many types of sterile medicinal solutions for various purposes, and it is particularly useful for injecting a patient directly with a needle which becomes harmless after use.

This object is achieved by the injection module according to the invention, characterized in that the sleeve consists of one rigid portion which interlocks with the barrel and is axially slidable over the barrel, and further in that the cylindrical barrel comprises a skirt which surrounds a needle-holder tip with at least one flexible tab cooperating with an annular interior rib in said rigid cylindrical sleeve to form an anti-return mechanism for the sleeve when it is in the advanced position, and at least one stop means that also cooperates with said annular interior rib in the sleeve and defines the path of the sleeve when it is in the advanced position.

In a first embodiment, said stopping means may consist of a rigid tab.

In a second embodiment, said stopping means may consist of a flexible tab.

According to a variation of the invention, the annular stopping means may consist of a protruding annular rib located at the end of said annular skirt.

According to yet another embodiment, said skirt may comprise two diametrically opposed flexible tabs and said stopping means may consist of a protruding annular rib extending across two diametrically opposed circular portions respectively located between said flexible tabs.

Said stopping means advantageously comprises a sharply angled side defining the protruding annular rib in relation to the skirt, and said annular interior rib on the sleeve is defined by sides forming acute angles with the interior sleeve wall.

The acute angles forming the sides with the interior sleeve walls preferably are lesser than or equal to 90° and are respectively complementary to the angle of the tip of the flexible tab and to the acute angle defining the protruding annular rib of the sleeve in relation to the skirt.

Advantageously, the flexible tab comprises a rounded rib opposite its sloped end which cooperates with the side of the interior rib when it is placed in the advanced position.

In the preferred embodiment, said sleeve is generally cylindrical in shape, with an interior diameter at the level of said interior annular rib generally equal to the exterior diameter of the cylindrical barrel.

According to various other embodiments, said sleeve may have rigid lateral walls, either completely sealed or with several openings arranged in a circle peripheral to said sleeve, said openings forming a passageway for the prongs of a gripping element on the skirt tabs.

The sleeve is further provided with handles extending laterally and symmetrically along at least one portion of the perimeter near one extremity, called the distal extremity, said handles comprising either two lateral flanges or an annular edge.

The aim of the invention is also achieved by a syringe such as that defined in the preamble, characterized in that said sleeve consists of one rigid piece, interlocked with and axially slidable on the barrel of the injector module, and further in that the cylindrical barrel of the injector module comprises a skirt surrounding the needle-holder tip, comprising at least one flexible tab cooperating with an annular interior rib on the rigid cylindrical sleeve, thereby forming an anti-return mechanism when the sleeve is in the advanced position, and at least one stopper means also cooperating with said annular interior rib on the sleeve and defining the path of the sleeve when it is in the advanced position.

The receptacle-propulsion module advantageously comprises said cylindrical barrel and a piston with a piston shaft engaged within the barrel.

According to a first variation, the propulsion-receptacle module comprises a reservoir that is closed at one end and sealed at the other end by a piston-valve-stopper connected to a transfer device comprising a tubular shaft connecting the reservoir with the needle.

According to a second variation, said receptacle-propulsion module comprises a receptacle that is closed at one end and sealed at the other end by a stopper, said stopper being designed to be perforated by a needle that is a double needle with one point located inside the cylindrical barrel.

According to a third variation, said receptacle module comprises a receptacle that is closed at one end by a stopper which receives a piston shaft, and at the other end by a membrane and a crimped capsule which can both be perforated by a needle that is a double needle with one point located inside the cylindrical barrel.

The present invention will be more readily understood with reference to the following description of several embodiments and to the attached drawings, wherein.

Figure 1:
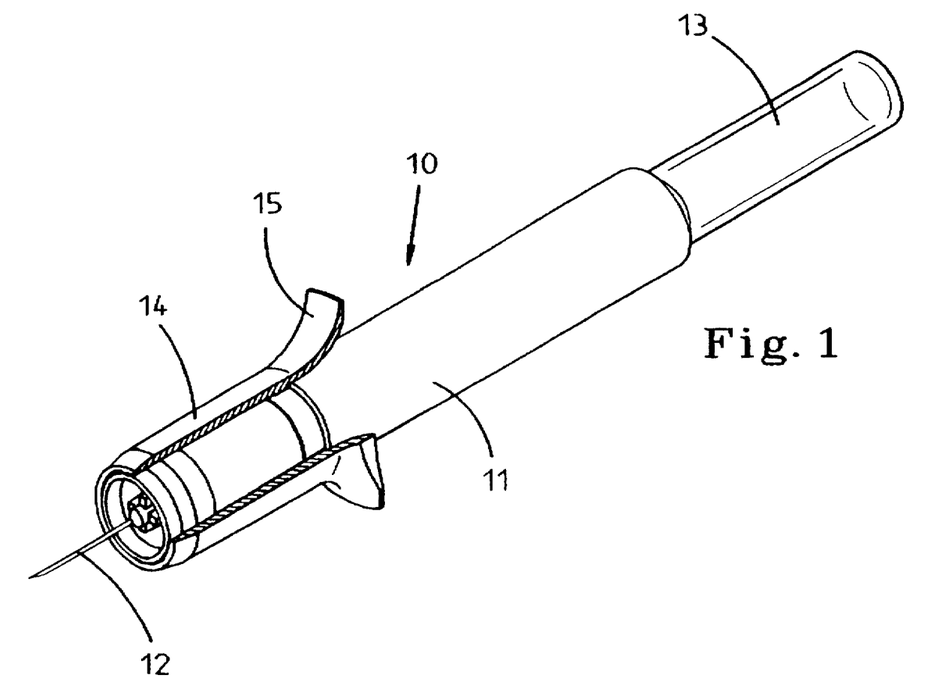
FIG. 1 is a perspective of a syringe according to the invention, ready for use.
Figure 2:
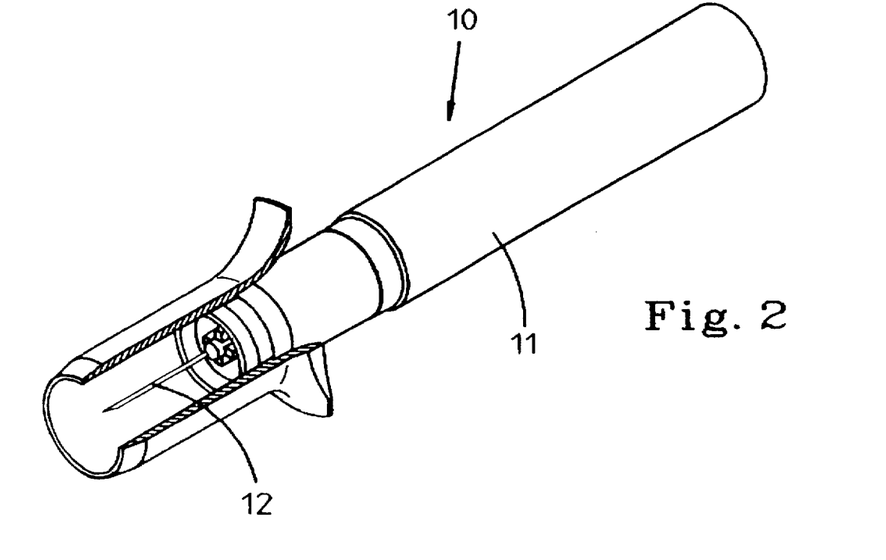
FIG. 2 is a view similar to FIG. 1, but after use.

With reference to FIGS. 1 and 2, syringe 10 comprises a cylindrical barrel 11 having a needle 12 extending from its proximate extremity and comprising a reservoir 13 for a medicinal substance. Reservoir 13 may comprise a single compartment if the syringe is the single component type, or it may comprise two compartments, each holding one component of a medicinal substance to be reconstituted. The reservoir has a second function—it acts as a piston shaft which the operator presses to propel the medicinal substance toward needle 12 for injecting a patient.

In addition, the syringe barrel has a rigid sleeve 14 for protecting the needle, cylindrical and coaxial with the barrel, which is movable between the retracted position shown in FIG. 1 and the advanced position shown in FIG. 2. This sleeve has handles and finger grips, 15 which may consist of flanges or of a circular crown forming a unit with the sleeve. In fact, the sleeve fitted with flanges is actually one piece of molded or injection-molded synthetic material which is placed on the syringe barrel after it is assembled and the reservoir is filled. This is an extremely advantageous method for manufacturing this type of pre-filled syringe. All the assembly and fitting operations, except for positioning the flanged sleeve, actually take place on uniformly cylindrical units. Therefore, all these operations can be performed on elements which are tightly packed together in an orderly fashion. Furthermore, the assembly and filling operations can take place on standard high capacity units and at very high speeds, since the intervening stages in which the components move from an orderly state to disorder, and the reverse, are eliminated. As a result, combining the flanges, which are necessary for comfort and efficiency when using the syringe, with the sleeve designed to protect the syringe operator from accidental sticks with a used needle, i.e., one which has been contaminated by the patient, not only resolves the problems of safety and comfort during use, but also considerably improves manufacturing productivity.

Barrel 11, needle 12 and needle protecting sleeve 14 constitute the injector module that is one of the sub-assemblies of the syringe. Reservoir 13 and a stopper acting as a piston (not shown in FIGS. 1 and 2) constitute the propulsion-receptacle module, which is another sub-assembly of the syringe.

Figure 3:
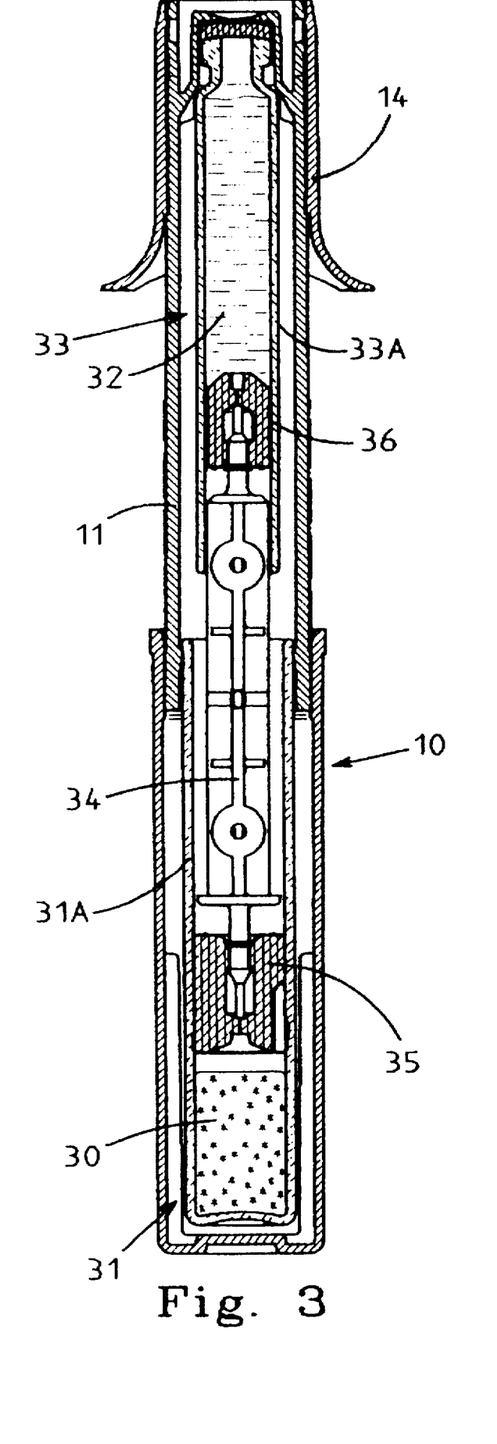
FIGS. 3 and 4 are axial cross-sections of a two-component syringe, ready for use and after use, respectively.
Figure 4:
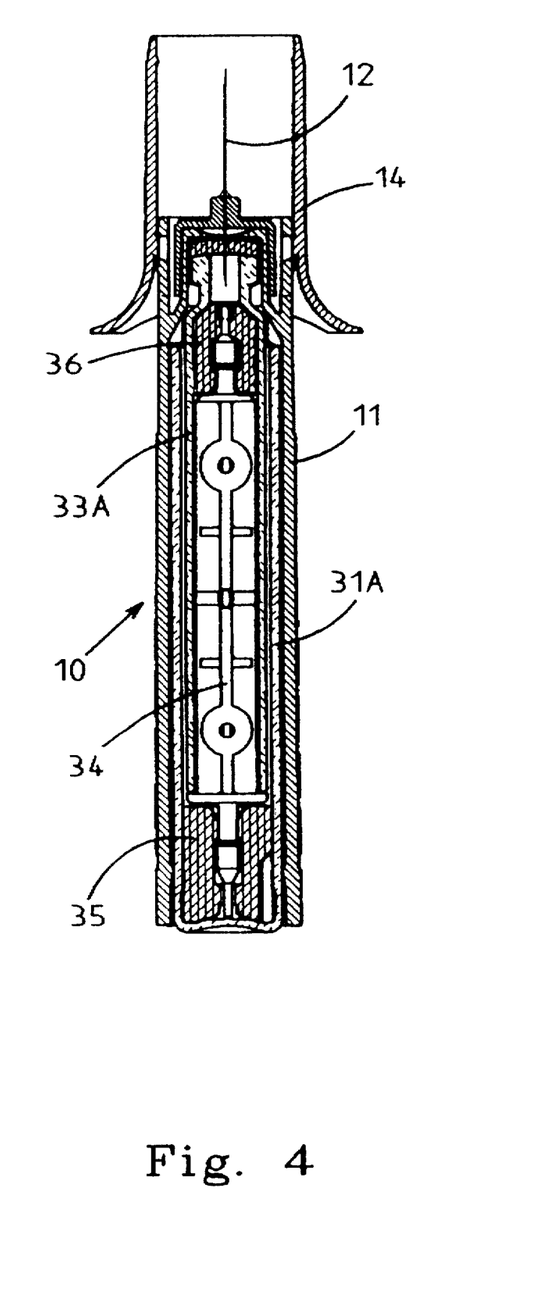

FIGS. 3 and 4 show an embodiment wherein syringe 10 is a two-component syringe, wherein one component 30, which may be a powder or a lyophilized substance, for example, is contained in one compartment 31 and a second liquid component 32 is contained in a second compartment 33. The unit formed by these two compartments 31 and 33 constitutes the reservoir of injectable medicinal substance. In this embodiment, the receptacle is composed of two cylindrical reservoirs 31A and 33A, telescopically interlocked, as shown more particularly in FIG. 4. These two cylindrical reservoirs 31A and 33A are connected by a transfer tube 34 and at least partially attached inside the cylindrical syringe barrel 11. In the first phase, transfer tube 34 transfers liquid component 32 into compartment 31 to dissolve solid component 30, and thereafter transfers the resulting solution to needle 12. The two compartments are respectively closed during the storage phase by two piston-valve-stoppers 35 and 36, respectively. During storage, they act as stoppers. In the first step of the active phase, the two components are mixed to reconstitute the medicinal substance which constitutes the injectable solution. During the next step of the active phase, the mixture is injected into the patient. After use, sleeve 14 is pushed to the advanced position as shown in FIG. 4 and as previously described. In this position it effectively protects the user from an accidental needle stick. As in the embodiment described previously, the injector module consists of barrel 11, previously provided with needle 12 attached to a needle-holder tip, and rigid protective sleeve 14. As for the propulsion-receptacle container, it consists of cylindrical reservoirs 31A and 33A, transfer shaft 34, and two piston-valve-stoppers 35 and 36.

Figure 5:
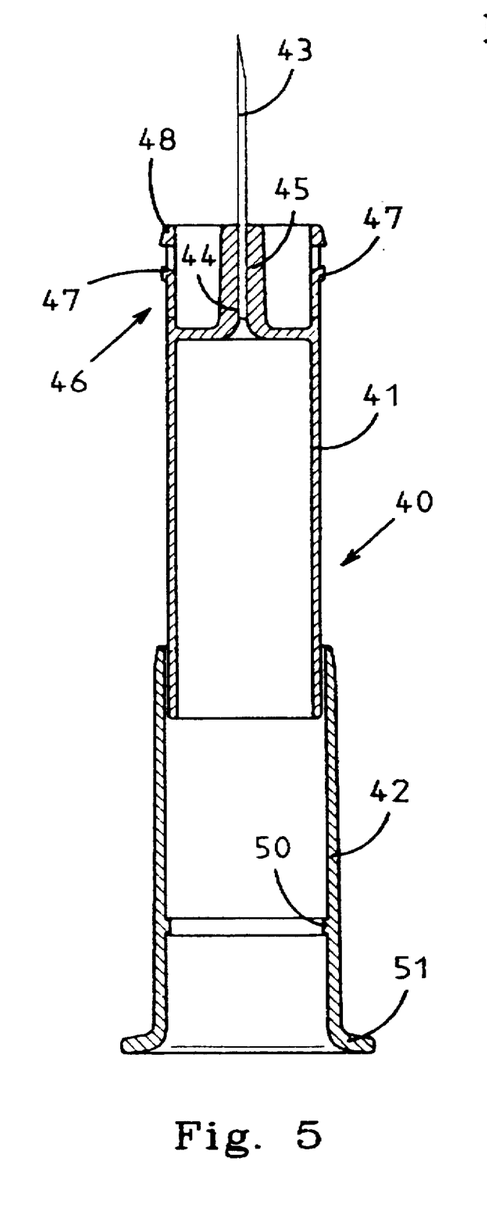
FIGS. 5, 6 and 7 are schematic representations of one embodiment of an injector module for a syringe according to the invention, with FIG. 5 illustrating the phase during which the sleeve is attached behind the barrel of the module, and FIG. 6 being a perspective of the annular skirt on the barrel, and FIG. 7 showing the position of the protective sleeve for the needle.
Figure 6:
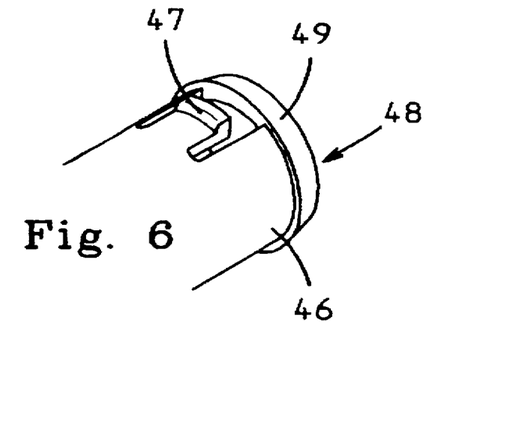
Figure 7:
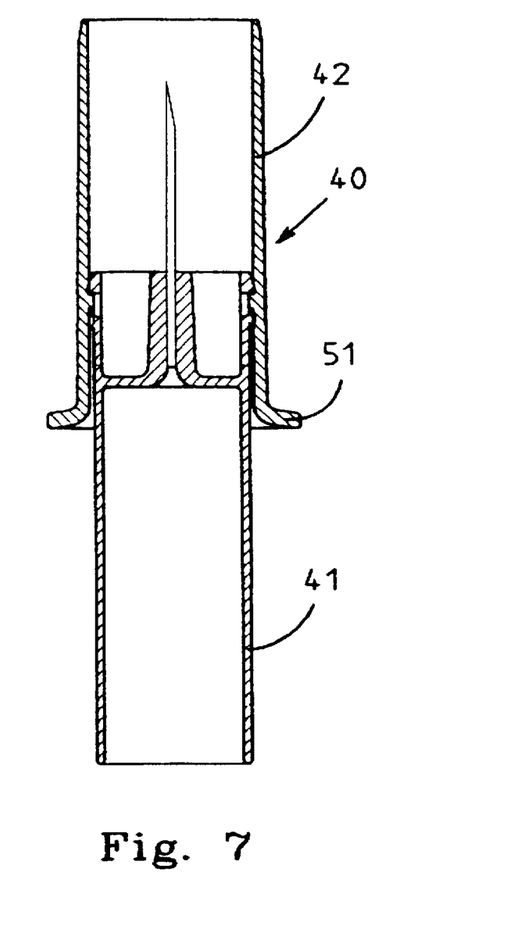

FIGS. 5, 6, and 7 are schematic representations of an injector module 40 for a syringe essentially comprising a cylindrical barrel 41 and a rigid sleeve 42 to protect the needle, cylindrical and coaxial with the barrel. The sleeve is attached to the rear of the barrel, that is the distal extremity opposite the proximate extremity supporting needle 43, within an appropriate duct 44 formed inside needle-holding tip 45. The propulsion-receptacle module is not shown. It may be designed in various ways to form either a disposable syringe or a pre-filled syringe with an independent reservoir acting as a piston shaft. The proximate end of the barrel of the module has an annular skirt 46 comprising at least one, but preferably two or more, flexible tabs 47 which are fairly elastic and which, when at rest, protrude slightly toward the outside Additionally, the proximate extremity has a stopper means 48, in this embodiment consisting of an annular rib 49, protruding toward the exterior, and defining an annular edge which is generally perpendicular to said annular skirt 46.

The barrel of the module, the annular skirt with flexible tabs and its rib which serves as a blocking element, as well as the needle-holder tip, are formed as one unit and made from injected synthetic material.

Sleeve 42 comprises an annular interior rib 50 and two lateral flanges or, preferably, an annular rib 51 which serves as a grip for the user's fingers during injection.

This sleeve is designed to be positioned at the distal end of the barrel of the module. At the level of the rib, 50 its interior diameter is equal to or greater than the exterior diameter of the barrel of the module, so it slides easily toward the proximate extremity. When the rib, which is rigid like the sleeve unit, reaches the level of the tabs, the flexible tabs retract inside the annular skirt until the rib contacts the annular edge defined by annular rib 49 which acts as a block. Since the distance between the end of the flexible tabs and said annular edge is generally equal to or slightly larger than the span of annular rib 50, the flexible tabs straighten after annular rib 50 passes, so that sleeve 42 is immobilized in the position shown in FIG. 7. The needle is completely retracted and the needle-protecting sleeve protects the operator from an accidental needle stick after the syringe has been used.

Figure 5A:
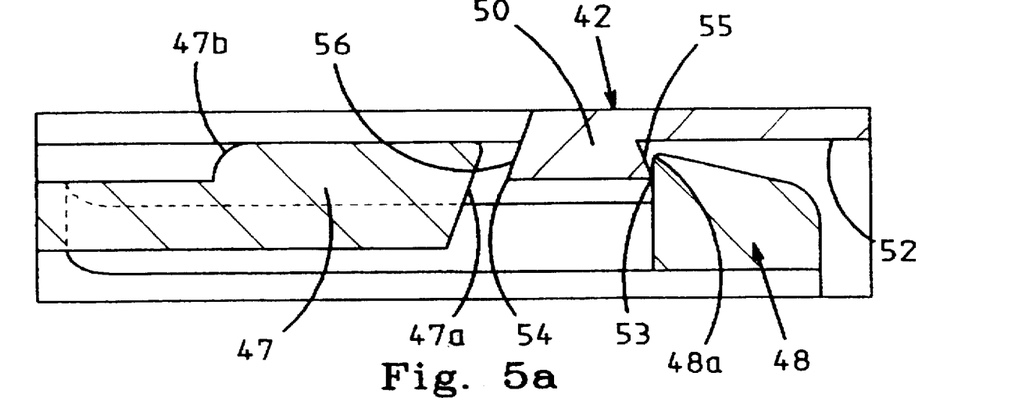
FIG. 5A is an enlargement of the detail of the flexible tabs on the barrel and an interior rib on the sleeve.

As shown in enlarged view 5A, the interior diameter 52 of sleeve 42 is approximately the same on either side of annular interior rib 50, so that the sleeve can be attached to either the front or the rear. This interior rib 50, which is not a molded unit, but rather two interlocking metal hubs arranged on either side of the rib, comprises acute angles 53 and 54. These acute angles 53 and 54, which are equal to or less than 90°, are connected to the interior diameter 52 of sleeve 42 by equivalent sides 55 and 56 which are slanted so that flexible tabs 47 and stop means 48 can engage completely when sleeve 42 is in the advanced position, as shown in FIG. 7.

In order to cooperate with side 56, one extremity 47a of flexible tabs 47 forms an angle with the longitudinal axis of the corresponding tab, which is generally complementary to the acute angles of interior rib 50 on sleeve 42, thereby preventing the sleeve from returning.

Similarly, stop means 48 may comprise an acute angle 48a which may range from 30° to 90° to cooperate with slanted side 55 of interior rib 50.

Opposite the extremity 47a of each tab there is an edge 47b, either sloping, conical or rounded, which in the present case is shaped somewhat like a quarter circle. This rounded edge cooperates with side 55 of interior rib 50 when the sleeve is pushed into the advanced position. Because of this rounded edge, the interior rib forces the flexible tabs toward the inside of the syringe so the sleeve can be positioned.

Figure 5B:
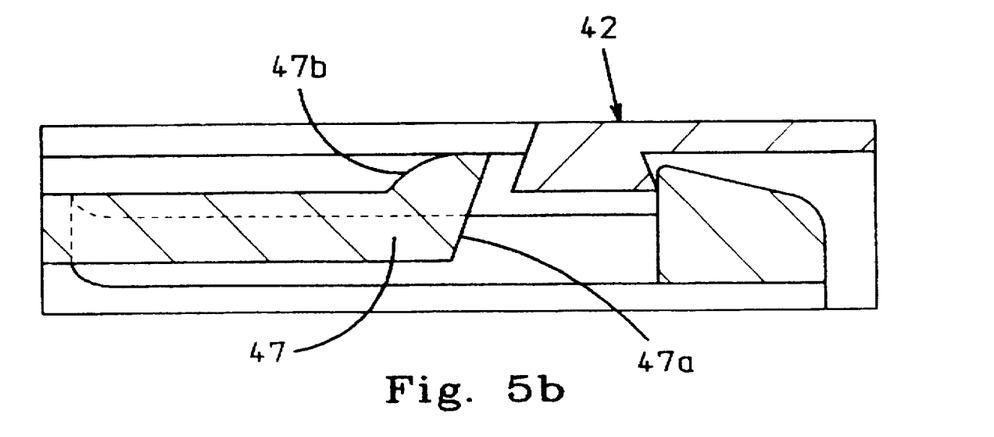
FIG. 5B shows a view similar to that of FIG. 5A, but of a different design.

FIG. 5B shows a variation in which the shape of edge 47b is a little different, inasmuch as it has a broader curve. Furthermore, the end portion of tab 47, which is defined on one side by rounded edge 47b and on the other by extremity 47a, is shorter in Figure B than in Figure A.

Figure 5C:
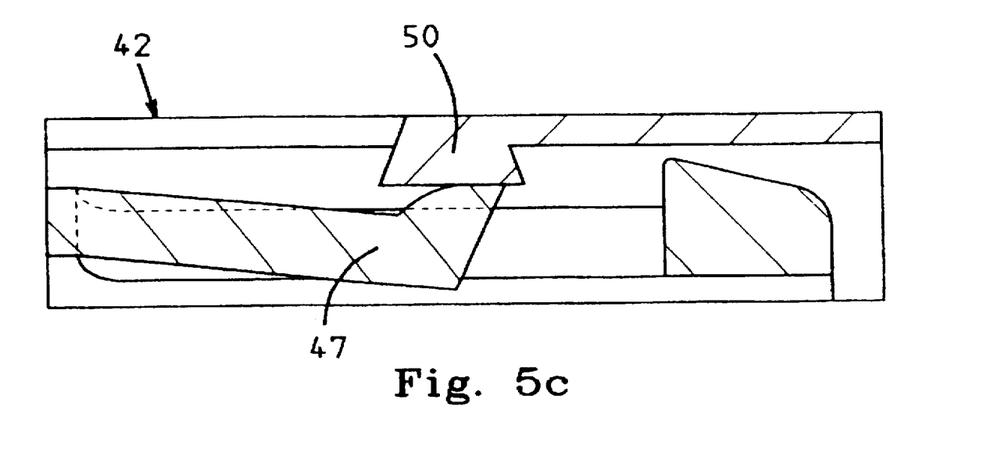
FIG. 5C illustrates how the flexible tabs and the interior rib function.

FIG. 5C shows the cooperation of tabs 47 with interior rib 50. At the moment the rib passes by, the tabs retract elastically and resume their initial position, thereby blocking sleeve 42 in position.

Besides controlling retraction of the tabs, the end portion constitutes a guide, since after interior rib 50 has passed by, the tabs spring back elastically and contact the interior sleeve wall, thus effectively guiding the sleeve.

Since interior rib 50 with acute angles 53 and 54 interlocks perfectly with flexible tabs 47 and stop means 48, which also has complementary acute angles, this ensures that the unit is irreversibly locked in the advanced position as shown in FIG. 7.

Figure 8:
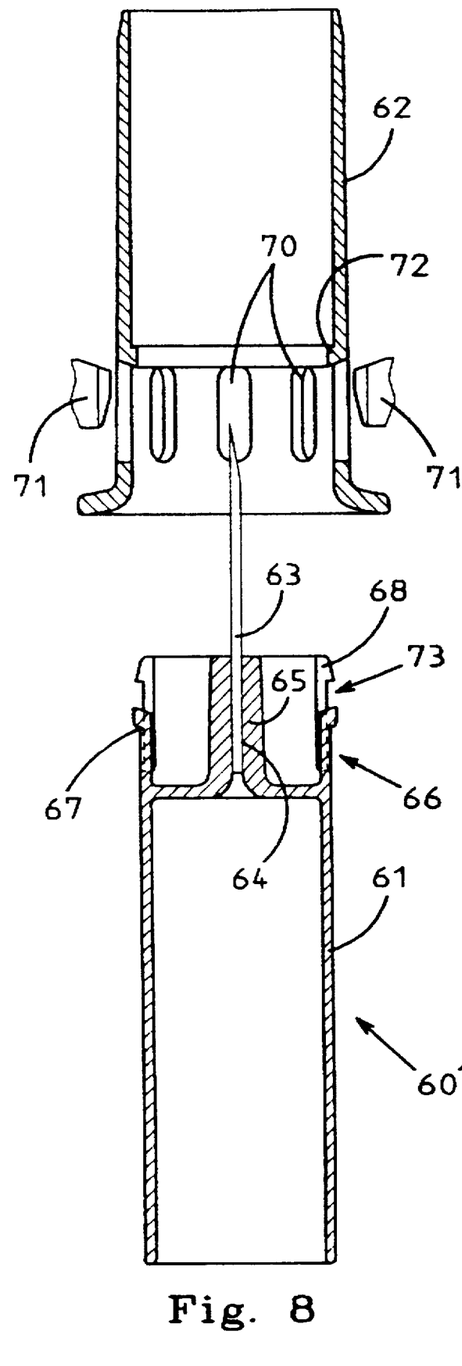
FIGS. 8, 9 and 10 are views of another variation of the injector module for a syringe according to the invention, wherein the sleeve is attached at the front of the barrel, similar to the views in FIGS. 5, 6 and 7.
Figure 9:
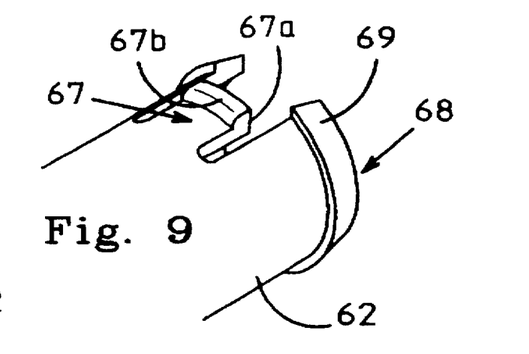
Figure 10:
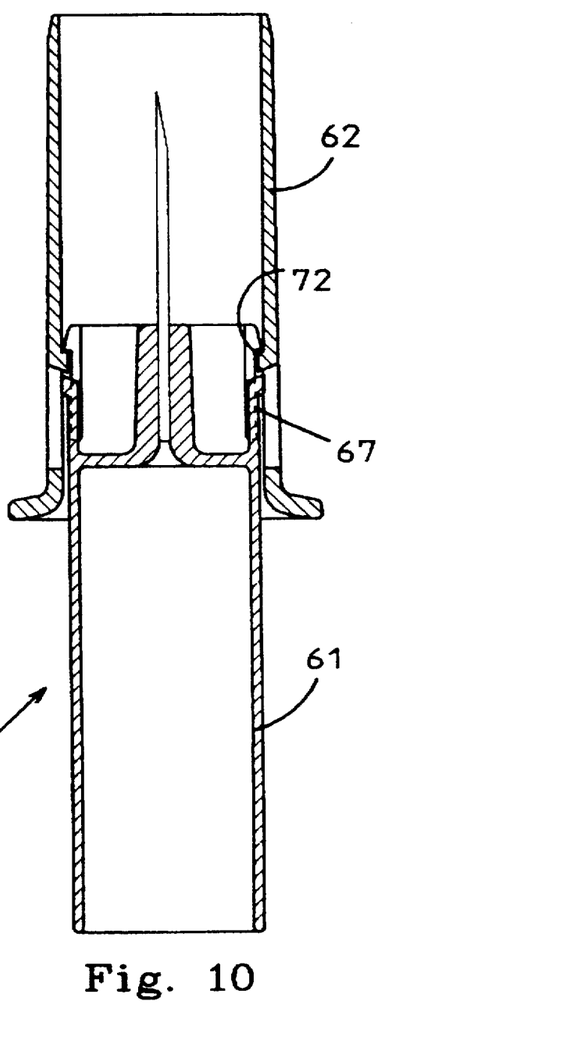

These specific interlocking designs can also apply to all the sleeves and to the annular skirt elements shown in the other drawings FIGS. 8, 9 and 10 show another embodiment of an injector module 60 for a syringe, comprising, as before, a cylindrical barrel 61 and a protective sleeve 62 for the needle 63 attached to duct 64 in needle-holder tip 65. As in the preceding design, the proximate extremity of barrel 61 has an annular skirt 66 with flexible tabs 67 and a stop means 68 consisting of at least one flexible tab 69. This flexible tab 69 may also be rigid and may perform the same function as annular rib 49 described with reference to FIG. 6.

Sleeve 62 is designed for attachment to the front of barrel 61, that is, the proximate extremity thereof. Since the ends of tabs 67 protrude and would thus prevent attachment, the sleeve has openings 70 arranged in a peripheral circle on the sleeve for the prongs of a suitable gripping means, which temporarily crimps the tabs to allow rigid interior ring 72 to pass over flexible tabs 67 and stop means 68, consisting of at least one flexible tab. This intervention is necessary only while the sleeve is being positioned. When the syringe has been used, rigid ring 72, which is shaped like an interior rib, is located in the space 73 separating tabs 67 from stop means 68, thereby blocking the sleeve in position. As in the embodiment of FIGS. 5A, 5B and 5C, flexible tabs 67 have one slanted end 67a and one edge 67b which is either curved, conical or sloped.

Figure 11:
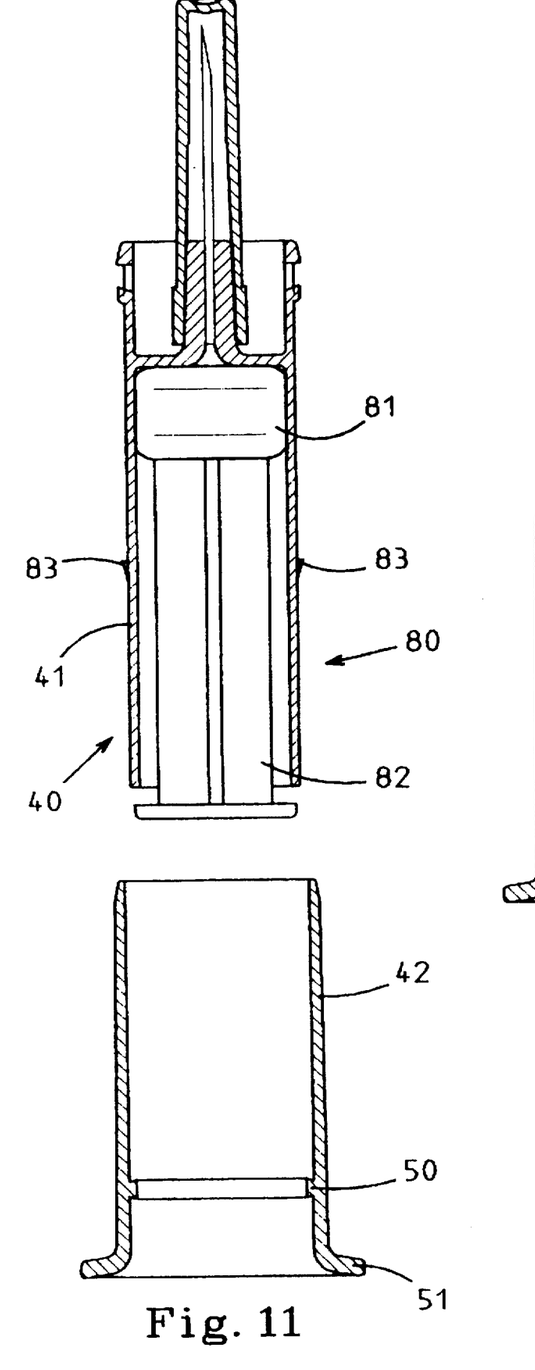
FIGS. 11, 12 and 13 show another embodiment of the syringe according to the invention, in which the sleeve is attached at the rear of the barrel.
Figure 12:
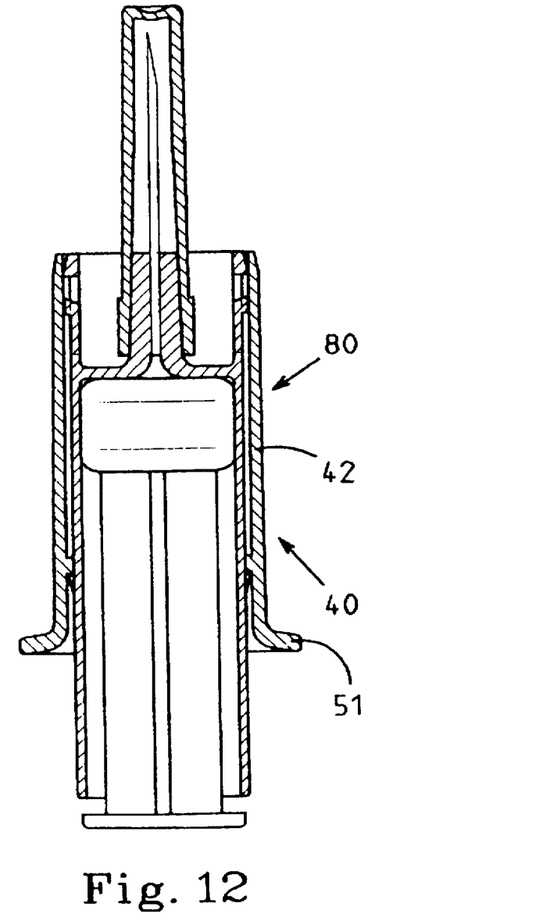
Figure 13:
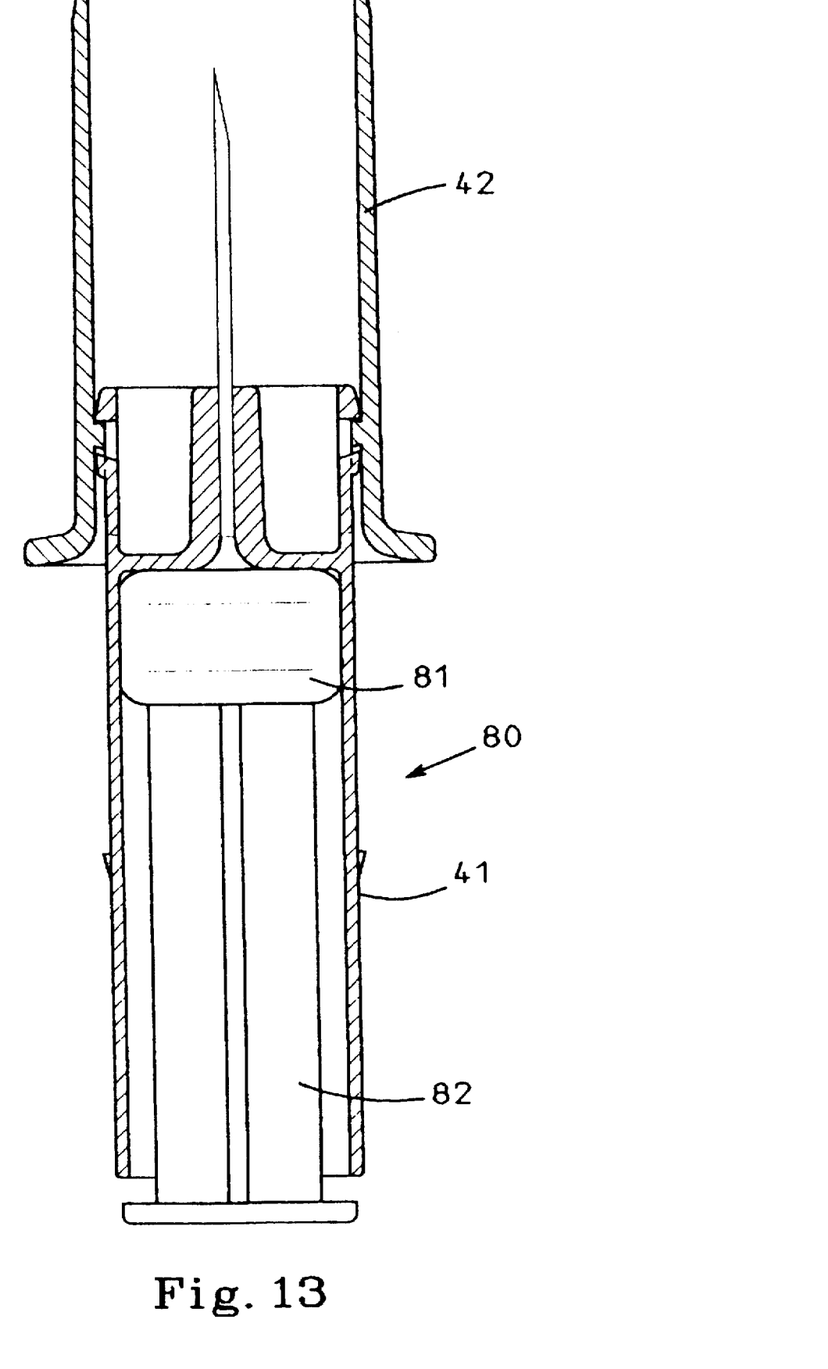

FIGS. 11, 12 and 13 show a disposable syringe provided with a sleeve attached to the rear, as described with reference to FIGS. 5, 6 and 7. In this case, syringe 80 is composed of injector module 40 and a propulsion-receptacle module formed by the interior portion of barrel 41, piston 81, and piston shaft 82. Sleeve 42 is attached to the distal end of barrel 41. The latter has at least one, but preferably several, blocking pins 83, which cooperate with interior rib 50 to prevent the sleeve from returning. This feature is indispensable, since sleeve 42 contains the flanges 51 which allow the operator to hold the syringe with two fingers and press the piston shaft with his or her thumb during injection. This position, in which the syringe is ready for use, is shown in FIG. 12. FIG. 13 shows the syringe after injection with the sleeve placed in the security position.

Figure 14:
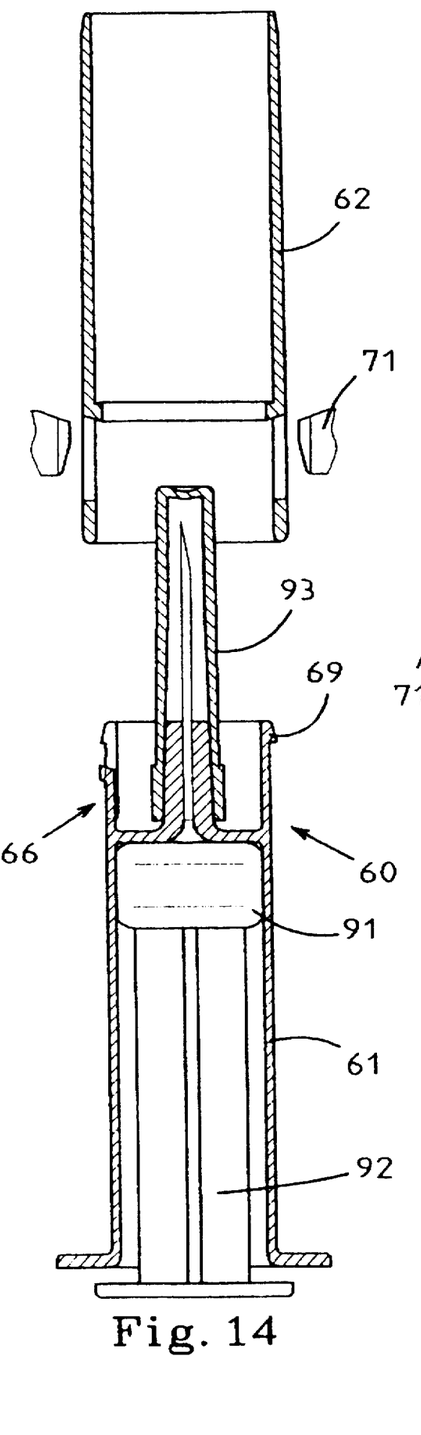
FIGS. 14, 15, 16 and 17 show another embodiment of the syringe according to the invention, in which the sleeve is attached at the front of the barrel.
Figure 15:
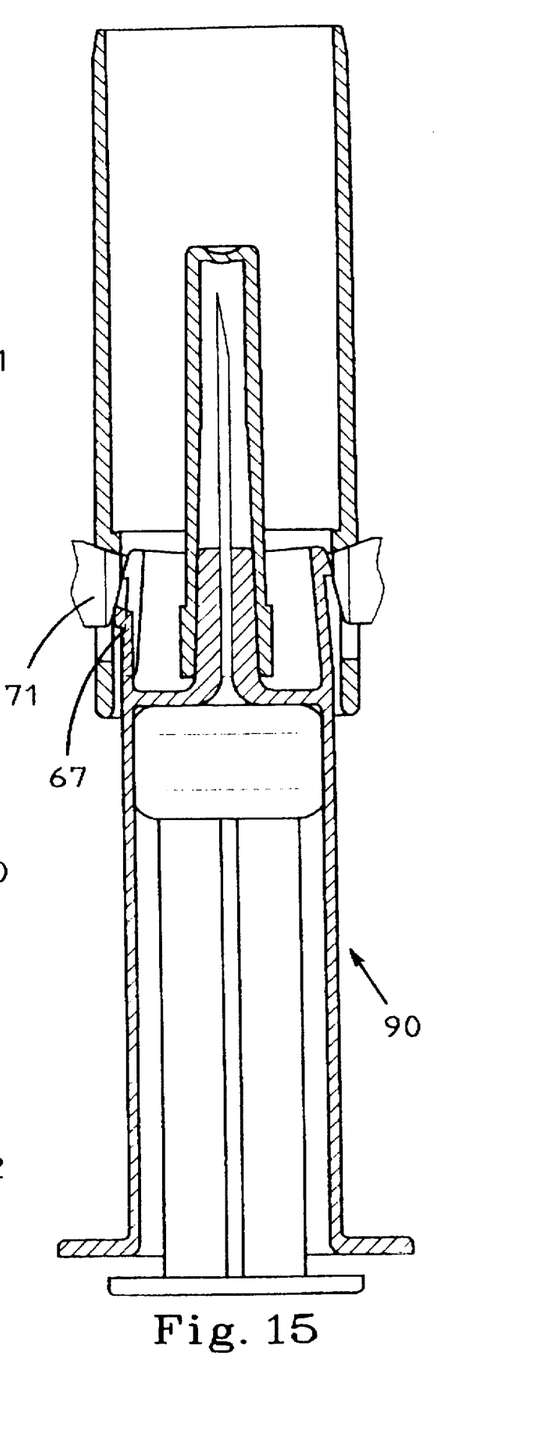
Figure 16:
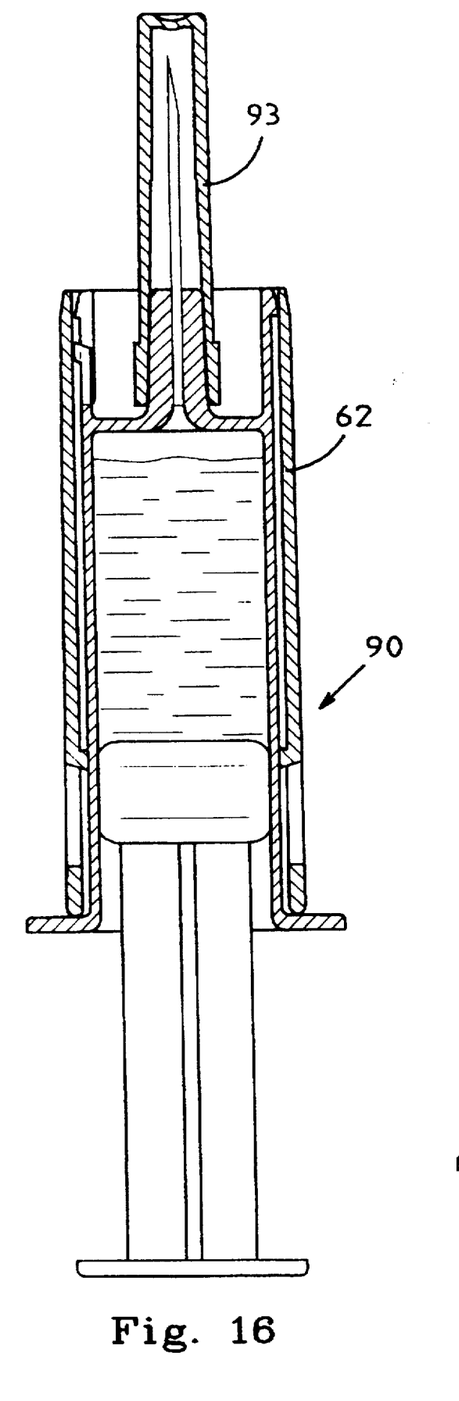
Figure 17:
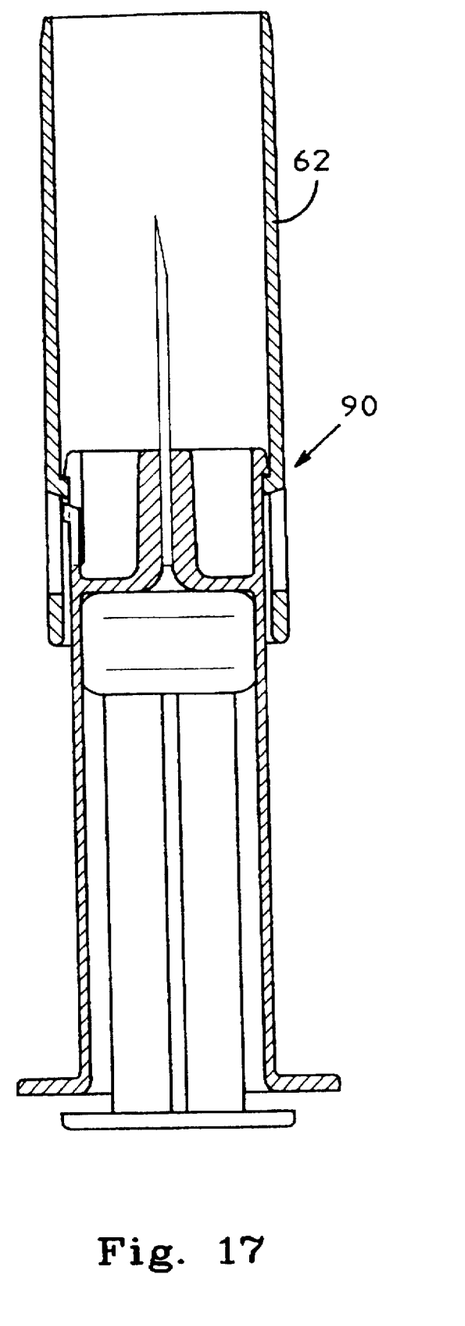
Figure 18:
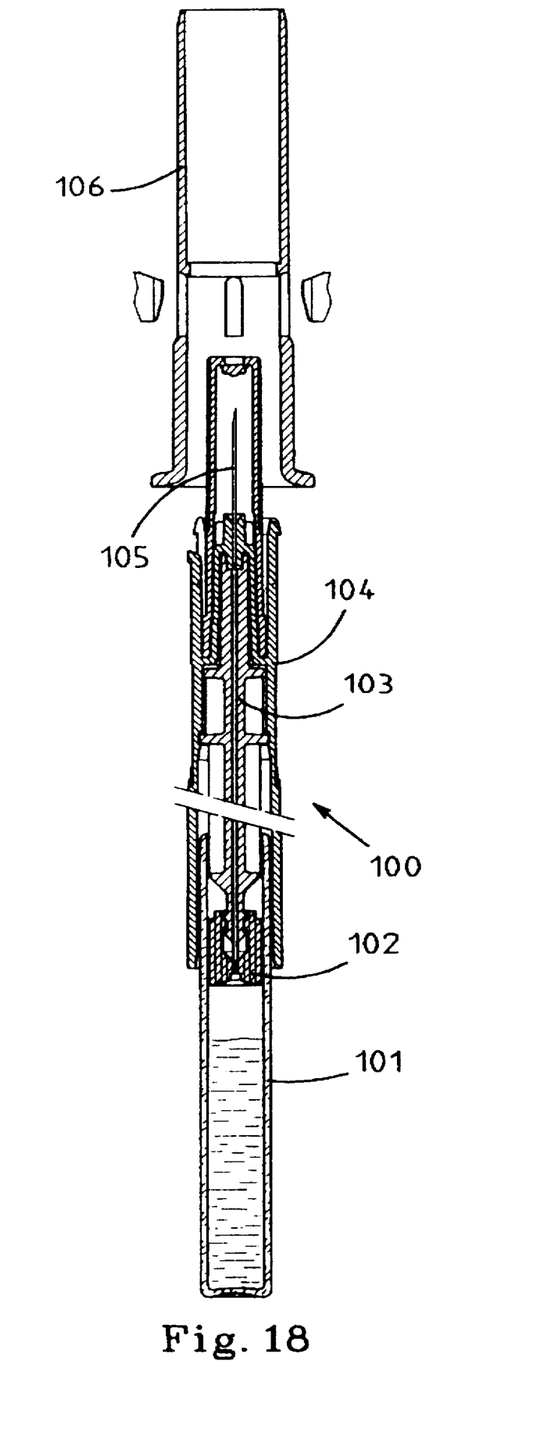
FIGS. 18, 19, 20 and 21 show a syringe design according to the invention in which the sleeve is attached at the front of the barrel.
Figure 19:
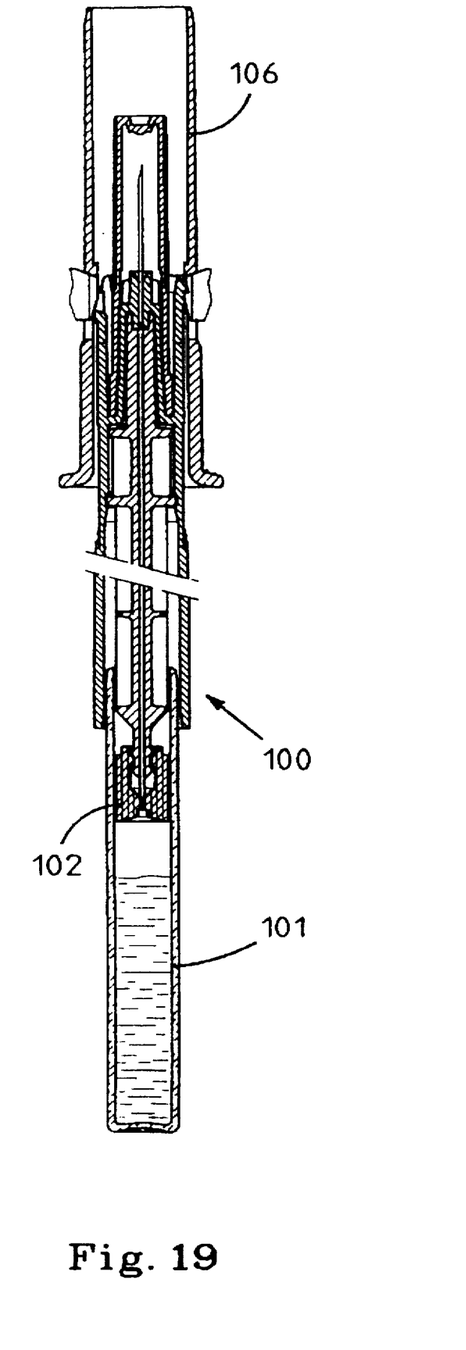

FIGS. 14, 15, 16 and 17 show a disposable syringe with a sleeve attached to the front, that is, the distal extremity of the barrel, as described with reference to FIGS. 8, 9 and 10. Syringe 90 consists of injector module 60 and a propulsion-receptacle module which, as in the example in FIGS. 11, 12 and 13, is formed of the interior portion of barrel 61 and a piston 91 attached to a piston shaft 92. Furthermore, in this case the needle is protected by a cover 93. Obviously, such a cover could be adapted to a disposable syringe 80 (see FIGS. 11, 12 and 13). FIG. 14 shows the first phase in positioning sleeve 62 on barrel 61. FIG. 15 shows a subsequent phase during which prongs 71 push back flexible tabs 67 on annular skirt 66 and/or the portions of the annular skirt comprising the annular rib 69, forming at least one flexible tab. FIG. 16 shows this syringe, which will be ready for use when cover 93 has been removed. FIG. 17 shows this syringe after use, with the sleeve in position to protect the user.

Figure 20:
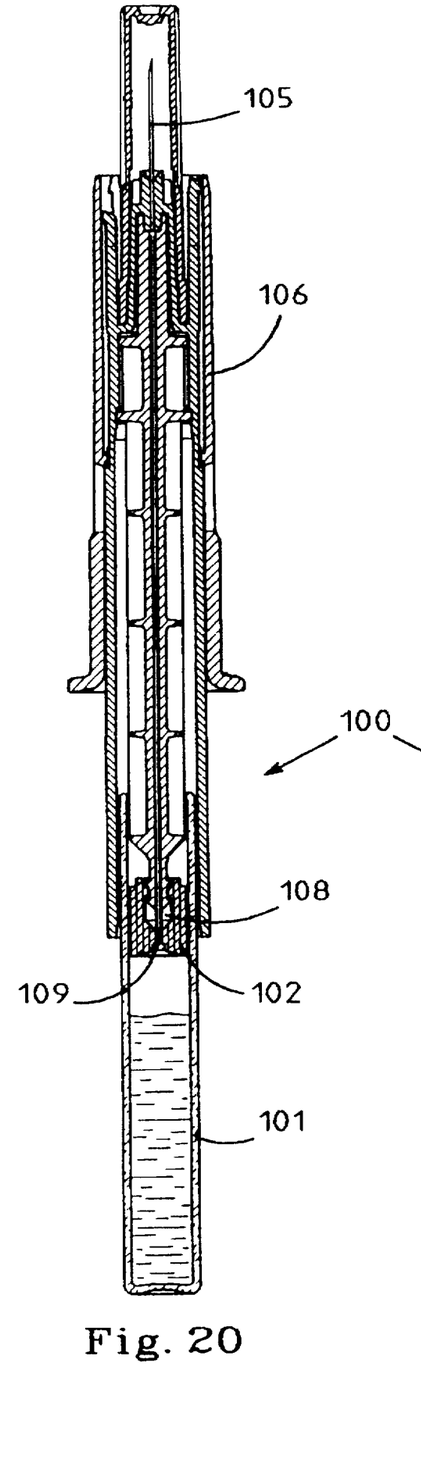
Figure 21:
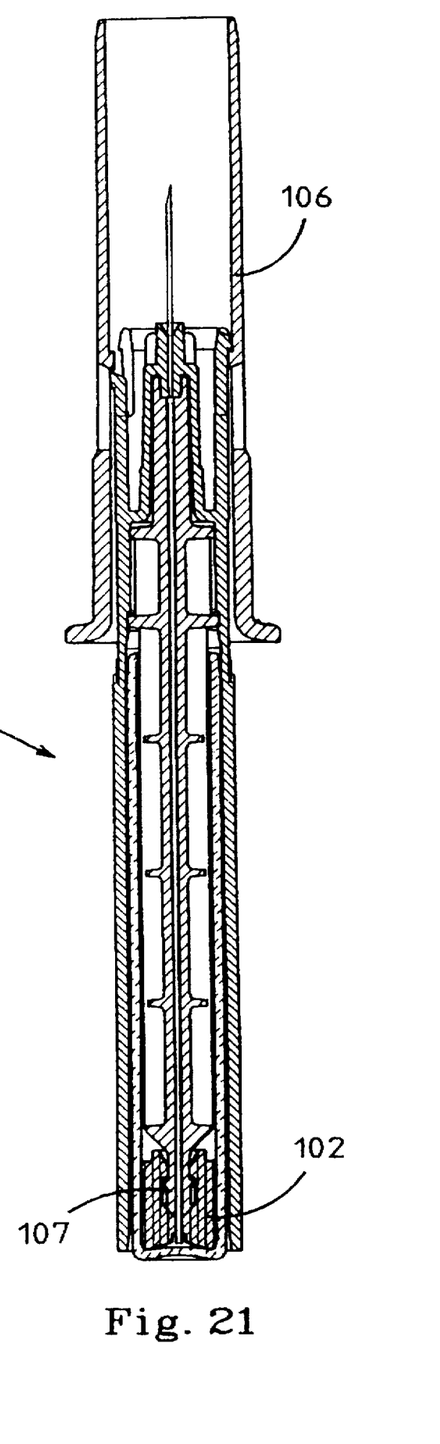

FIGS. 18, 19, 20 and 21 show a syringe 100 which is a pre-filled single component syringe with a sleeve attached to the proximate end of the barrel. This syringe comprises an injector module similar to that described with reference to FIGS. 8 through 10. However, in this case the propulsion-receptacle module comprises a reservoir 101, preferably made of glass or the like, closed at one end and blocked at the other end by a piston-valve-stopper 102, and a transfer device 103 inside barrel 104 of the injector module. In the initial phase, the transfer device, which essentially consists of a tubular shaft communicating between the interior of reservoir 101 and needle 105, is not connected to piston-valve-stopper 102. This device acts as a stopper. After sleeve 106 has been placed on the proximate end (see FIG. 19), the syringe is ready for storage. This stage is shown in FIG. 20. FIG. 21 shows the syringe after use, with the sleeve in the advanced position. Between these two phases, the syringe is prepared for use by pushing the reservoir so that the transfer device connects to piston-valve-stopper 102. This connection is accomplished when tip 107, integral with the corresponding end of the transfer device, engages in central cavity 108 of the piston-valve-stopper 102 and the end of the tubular shaft on this device passes through a hole 109 formed in said piston-valve-stopper. When this end penetrates the linear opening, which is fairly tall, needle 105 can communicate directly with the interior of reservoir 101. Note that the thickness of the opening ranges from ⅕ to ½ the width of the piston-valve-stopper 102, and that height is approximately 1 mm larger than the diameter of the end of the tubular shaft, so that lateral pressure on its lips seals the stopper tightly during storage.

Figure 22:
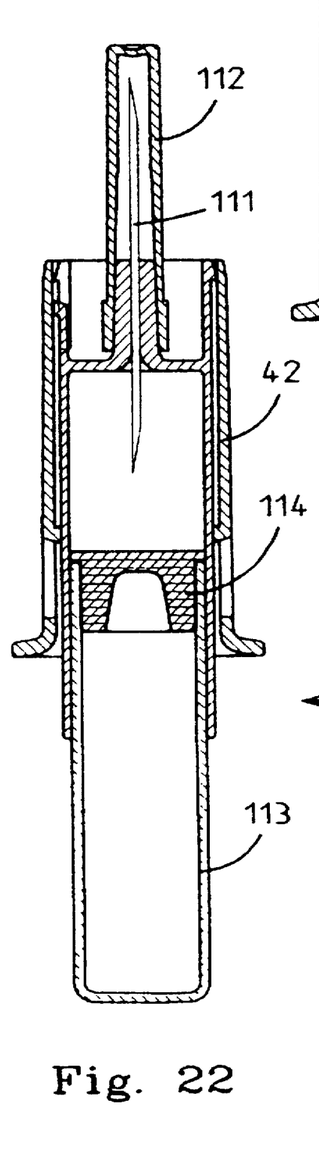
FIGS. 22, 23 and 24 show a blood testing syringe with the sleeve attached to the front.
Figure 23:
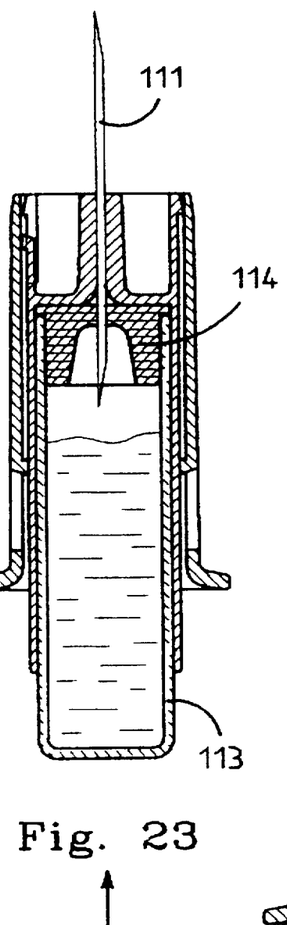
Figure 24:
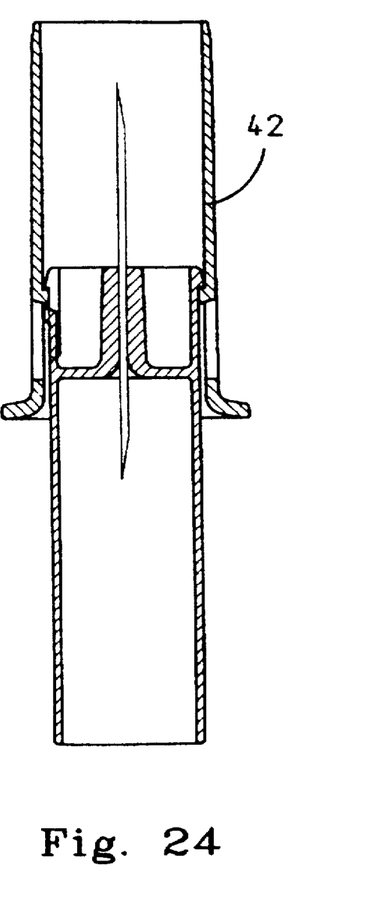

FIGS. 22, 23 and 24 show a blood testing syringe 110. This syringe comprises an injector module essentially identical to that described with reference to FIGS. 5, 6 and 7. However, the needle 111 is a double needle and is protected by a cover 112. An empty air vial 113, sealed by a stopper 114, forms the propulsion-receptacle module in this case; it is used to aspirate and hold the patient's blood in a conventional blood testing procedure, while stopper 114 is designed so that needle 111 can perforate it. FIG. 22 shows the syringe before use, FIG. 23 shows the syringe during use, and FIG. 24 shows it after use, when sleeve 42 has been moved to the advanced position where it protects the operator, and the filled vial has been removed.

Figure 25:
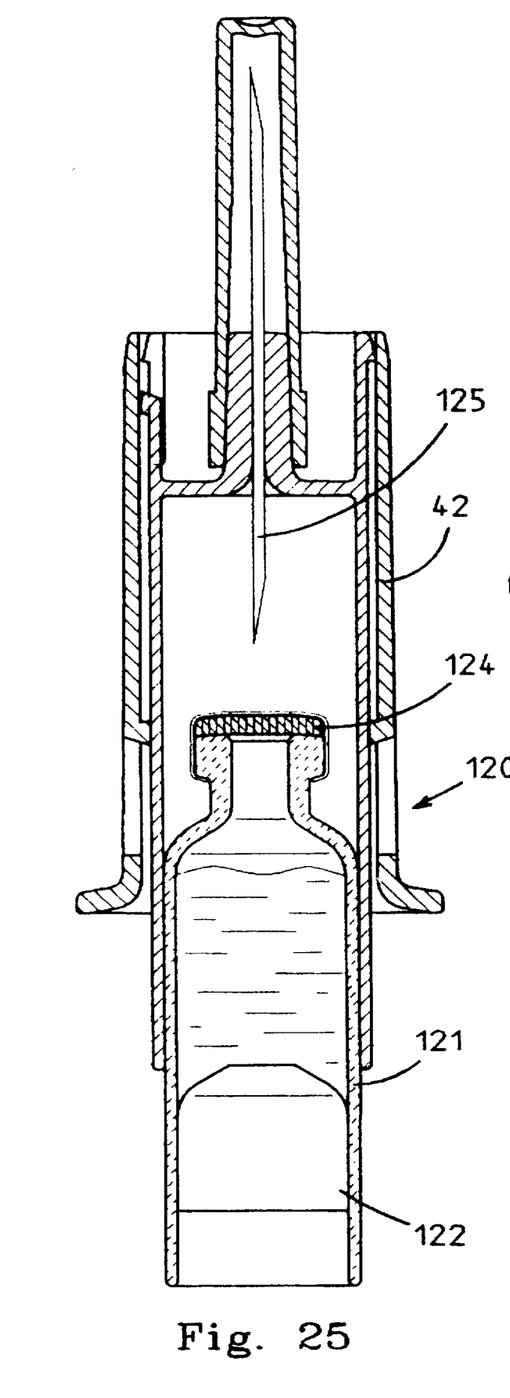
FIGS. 25 and 26 show a dentary carpal type syringe in which the sleeve can adapt to either the front or the rear of the barrel as required.
Figure 26:
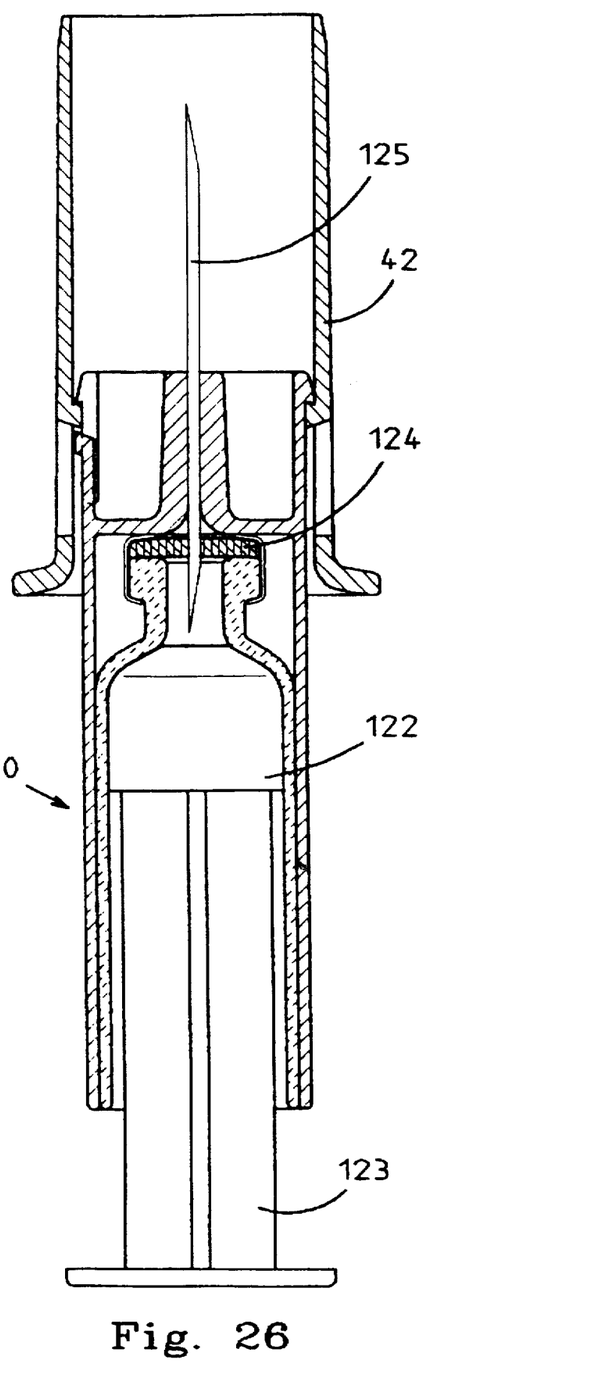

FIGS. 25 and 26 show a specialized syringe 120 comprising a dentary carpal syringe 121. The injector module is similar to those of FIGS. 22, 23 and 24. The empty air vial is replaced by the dentary carpal 121. This consists of a vial sealed at one end by a membrane and a capsule 124 which can be perforated by double needle 125 and the base of the capsule is sealed by a stopper 122 which acts as a stopper during storage (see FIG. 25) and acts as a piston when it is associated with a piston shaft 123 (see FIG. 26).

As in the previous examples, after use, sleeve 42 is pushed into the advanced position to protect the user from an accidental needle stick.

All these embodiments demonstrate that whether the sleeve is placed on the distal extremity or the proximate extremity, it can be moved to the advanced position after the syringe is used, effectively protecting the medical technician. In addition, since there are flanges for gripping the syringe and its other components are cylindrical without any protruding exterior elements, the units can be assembled (and pre-filled and sterilized, if required) when prepacked, as the flanged sleeve can be added later. This facilitates product manufacture greatly and reduces costs substantially.

I claim:

1. An injector module having a syringe subassembly, said module comprising:

a cylindrical barrel having a distal and proximate extremity;

a needle extending from said proximate extremity and attached to said barrel by a needle-holder tip;

a sleeve being movable between a retracted position, exposing said needle, and an advanced position, covering said needle, wherein said sleeve comprises a single rigid piece telescopically interlocked with and axially slidable on said barrel;

an annular skirt, attached to said proximate extremity, surrounding said needle-holder tip (45);

at least two diametrically opposed flexible tabs on said skirt that cooperate with an interior annular rib (50) on said rigid piece to form an anti-return device when said sleeve is in the advanced position; and at least one stop means also cooperating with said annular rib (50) on said sleeve thereby to define a path of said sleeve when said sleeve is in the advanced position, said stop means comprising an annular protruding rib extending across two diametrically opposed circular portions respectively located between said flexible tabs.

2. An injector module as defined in claim 1 wherein said annular protruding rib is located at an end of said annular skirt (46).

3. An injector module as defined in claim 1 wherein said stop means (48) comprises an acutely angled side defining said protruding annular rib (49) in relation to said skirt (46).

4. An injector module as defined in claim 1 wherein said interior annular rib (50) on said sleeve (42) is defined by sides (55, 56) forming angles (53, 54) in relation to an interior wall of said sleeve (42).

5. An injector module as defined in claim 4 wherein said angles (53, 54) forming the sides with said interior wall are lesser than or equal to 90°.

6. An injector module as defined in claim 4 wherein said angles (54, 53) are respectively complementary to an angle of an extremity (47a, 67a) of each of said at least two flexible tabs and to an acute angle which defines said annular protruding rib (49) on said sleeve in relation to said skirt.

7. An injector module as defined in claim 1 wherein each of said flexible tabs (47, 67) comprise, opposite a slanted extremity thereof (47a, 67a), a curved edge (47b, 67b) cooperating with a side (55) of the interior rib (50) when the sleeve (42, 62) is placed in the advanced position.

8. An injector module as defined in claim 1 wherein said sleeve is generally cylindrical in shape, said sleeve further comprising, at a position substantially level with said interior rib, an interior diameter (52) that is generally equal to an exterior diameter of the cylindrical barrel (41).

9. An injector module as defined in claim 8 wherein said sleeve (42) has rigid lateral walls which are completely closed.

10. An injector module as defined in claim 8 wherein said sleeve (62) has rigid lateral walls with several openings (70) therein arranged about a peripheral circle on said sleeve in order for said openings to cooperate with prongs on a suitable gripping device.

11. An injector module as defined in claim 8, wherein said sleeve (42) has handles extending laterally and symmetrically along at least one portion of a perimeter of said distal extremity.

12. An injector module as defined in claim 11 wherein said handles consist of two lateral flanges.

13. An injector module as defined in claim 11 wherein said handles comprise an annular rim (51).

14. A prefilled syringe having at least one compartment for holding a medicinal substance that is to be reconstituted by mixing with another component, said syringe comprising (i) an injector module, which further comprises:

a cylindrical barrel having a distal and proximate extremity;

a needle extending from said proximate extremity and attached to said barrel by a needle-holder tip;

a sleeve being movable between a retracted position exposing said needle and an advanced position covering said needle, wherein said sleeve comprises a single rigid piece telescopically interlocked with and axially slidable on said barrel;

an annular skirt, attached to said proximate extremity, surrounding said needle-holder tip;

at least two diametrically opposed flexible tabs on said skirt that cooperate with an interior annular rib on said rigid piece to form an anti-return device when said sleeve is in the advanced position; and at least one stop means also cooperating with said annular rib on said sleeve thereby to define a path of said sleeve when said sleeve is in the advanced position, said stop means comprising an annular protruding rib extending across two diametrically opposed circular portions respectively located between said flexible tabs;

and (ii) a propulsion receptacle module, which further comprises:

at least one receptacle for defining said compartment, said receptacle being slidable within said barrel to act as a piston shaft; and at least one stopper for containing said medicinal substance within said receptacle, said stopper being slidable within said receptacle to act as a piston.

15. A syringe as defined in claim 14 wherein said barrel comprises a piston (81) and a piston shaft (82) engaged therein.

16. A syringe as defined in claim 14 wherein said receptacle comprises a reservoir (101), closed at one end and blocked at the other end by a piston-valve-stopper (102), connected to a transfer device (103) having a tubular shaft for communication between the reservoir and said needle (105) of the injector module.

17. A syringe as defined in claim 14 wherein said needle of the injector module is a double needle, with one point located inside said cylindrical barrel, and said receptacle comprises a container (113), closed at one end and blocked at the other end by a stopper (114), which can be perforated by said one point.

18. A syringe as defined in claim 14 wherein said needle (125) of the injector module is a double needle having one point thereof located inside the cylindrical barrel and said receptacle (121) is closed at one end by a stopper (122), said stopper designed to receive a piston shaft (123), and closed at the other end by a membrane and a crimped capsule which are capable of being perforated by said one point.

* * * * *